United States Patent [19]

Butler

[11] 4,347,888
[45] Sep. 7, 1982

[54] METHOD OF MAKING FORMS FOR INVESTMENT CASTING AND PRODUCTS PRODUCED THEREFROM

[76] Inventor: Melvyn P. Butler, Derby, England

[21] Appl. No.: 132,296

[22] Filed: Mar. 20, 1980

[51] Int. Cl.³ .............................................. B22C 7/02
[52] U.S. Cl. ...................................... 164/34; 164/35; 164/DIG. 4
[58] Field of Search ..................................... 164/34–36, 164/45, DIG. 4; 264/16, 19, 221, 226, 227, 317; 29/160.6

[56] References Cited

U.S. PATENT DOCUMENTS

| | | | |
|---|---|---|---|
| 1,150,102 | 8/1915 | Cruickshank | 164/34 |
| 3,375,582 | 4/1968 | Myerson | 164/34 X |
| 3,532,776 | 10/1970 | Kopp | 164/34 X |
| 3,661,198 | 5/1972 | Evenson | 164/34 X |

Primary Examiner—R. L. Spruill
Assistant Examiner—K. Y. Lin
Attorney, Agent, or Firm—Austin R. Miller

[57] ABSTRACT

A method of making a form of a desired shape, for use in an investment casting technique which comprises forming a first sheet of formable material to a shape which approximates to the desired shape of the form, disposing the formed shape around a layer of deformable hardenable material, applying a compressive force to the formed shape to deform the underlying hardenable material to a desired shape, hardening the hardenable material to produce a form precursor, removing the formed shape from the hardened form precursor and utilizing the hardened form precursor to form a second sheet of formable material into the form of the desired shape. The invention also includes a method of making crowns by an investment casting technique utilizing the form produced by this method.

17 Claims, 6 Drawing Figures

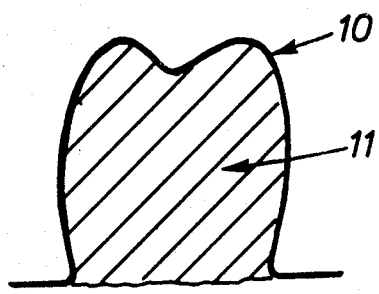
FIG. I
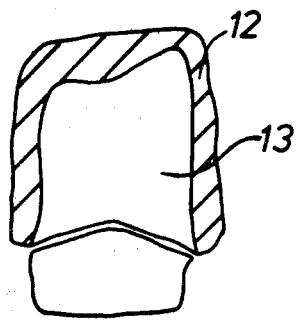
FIG. II
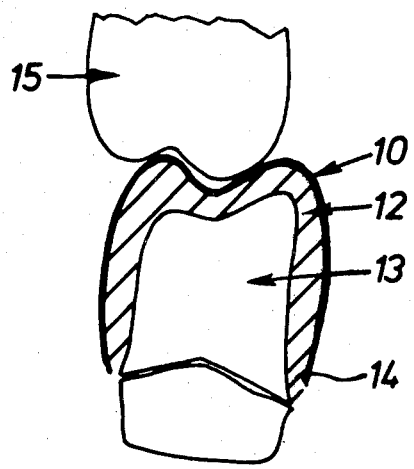
FIG. III
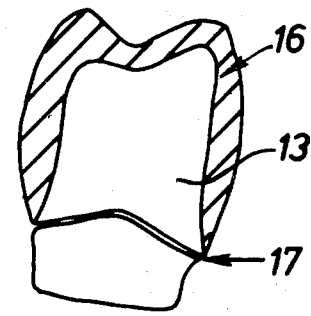
FIG. IV
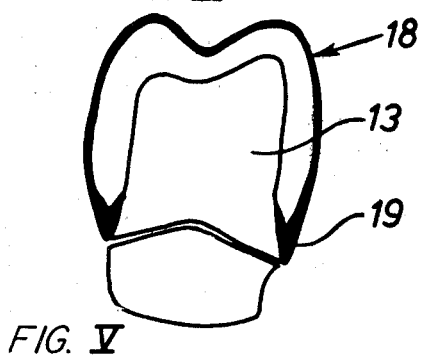
FIG. V
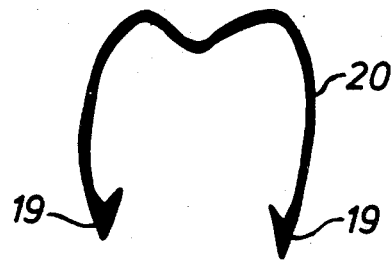
FIG. VI

METHOD OF MAKING FORMS FOR INVESTMENT CASTING AND PRODUCTS PRODUCED THEREFROM

This invention relates to the production of articles by investment casting techniques and to a method of making a form for use in investment casting techniques. More particularly the invention concerns a method of making crowns, such as gold crowns for teeth, and a method of making a form for use in making such crowns by an investment casting technique.

The conventional technique for producing crowns, such as gold crowns, utilizes an impression which is made by the dentist in a hardenable resilient material such as a hardenable rubber composition. This impression will include an impression of at least the teeth surrounding the one to be crowned and will also include an impression of the decayed tooth which has been ground down by the dentist in preparation for crowning.

This impression is then utilized, usually by a dental laboratory, to produce a crown. A plaster cast of the stump remaining after the dentist has ground down the decayed tooth is produced on a brass pin and a model of the teeth in that jaw is also cast in such a way that the stump can be removably located in it by means of the brass pin.

The next stage of the process is to cast a layer of wax on the stump and to carve the wax by hand to give the external shape of the desired crown. The carved shape will generally be such as to be compatible with the other teeth. After carving, a rod of wax, generally referred to as a sprue, is attached at one end to the carved wax and at the other end to a conical wax reservoir.

This assembly can then be used to produce a mold which is achieved by casting in an investment casting ring a heat-resisting investment compound with the wax reservoir at the base of the ring. When the plaster compound is set hard it is heated in a furnace to remove all the wax and subsequently a gold crown is cast by introducing molten gold through the sprue into the mold cavity formed by the carved wax.

According to one aspect of the present invention a method of making a form of a desired shape for use in an investment casting technique which comprises:
(a) forming a first sheet of formable material to a shape which approximates to the desired shape of the form;
(b) disposing the formed shape around a layer of deformable hardenable material;
(c) applying a compressive force to the formed shape to deform the underlying hardenable material to a desired shape;
(d) hardening the hardenable material to produce a form precursor;
(e) removing the formed shape from the hardened form precursor; and
(f) utilizing the hardened form precursor to form a second sheet of formable material into the form of the desired shape.

According to another aspect of the invention a method of making a crown for a tooth which comprises:
(a) forming a first sheet of formable material to a shape which approximates to a desired shape of the crown;
(b) applying a layer of hardenable material between a cast model of the tooth stump to which the crown is to be fixed and the formed shape from step (a)
(c) disposing the assembly of the cast model of the tooth stump, hardenable material and formed shape in a model of at least the teeth surrounding the tooth to be crowned and applying a compressive force to the assembly by means of a model of the occluding tooth or teeth in the jaw opposite to that in which the tooth to be crowned is situate to deform the underlying hardenable material to a desired shape;
(d) hardening the hardenable material to produce a crown form precursor;
(e) removing the formed shape from the hardened crown form precursor;
(f) utilizing the hardened crown form precursor to form a second sheet of deformable material into a crown form of the desired shape of the crown;
(g) producing an investment casting mold from the crown form of step (f) and burning out the crown form; and
(h) casting the crown in the investment casting mold.

Conventionally, the first sheet is formed by means of a deep-drawing technique. The second sheet may also be formed by a deep-drawing technique.

Advantageously, additional material is added to the second formed sheet in order to produce the final desired shape of the form. Preferably the additional material is wax.

In one method according to the present invention a plaster model of the teeth in one jaw and a plaster cast of the stump of the tooth to be crowned is produced in the conventional way. An artificial tooth is then chosen from a selection of stock teeth to match approximately the remaining teeth in the mouth. Supplies of such stock teeth are readily available as they are used in the preparation of dentures. When a stock tooth of the desired shape is selected it is used to make a first plastics impression in a sheet of formable plastics material. This can be effected by a process known as deep-drawing in which the sheet is heated to a temperature at which it is formable and the stock tooth pushed into it. Usually a backing of a deformable material which will control the forming of the plastics sheet is employed for this step.

The first plastics impression, which is a female mold of the approximate shape of the desired tooth, is then cut from the sheet of plastics material filled with hardenable material and pressed on to the plaster cast of the stump. The stump is then inserted in the model of the teeth in that jaw and a model of the teeth in the other jaw impressed upon it so that the occluding tooth on the opposite jaw can depress contacting areas of the plastics impression. The hardenable material is then allowed to harden on the plaster cast of the stump.

The plastics impression is then removed and discarded and any excess of hardenable materal around the margin of the stump is removed to give a smooth surface. The smooth hardened material at this stage is in the shape of the desired crown but is smaller by an amount governed by the thickness of the material of the first plastics impression, and is referred to herein as the crown form precursor.

The crown form precursor is then used to produce a second plastics impression by a method of deep-drawing as described above. The plastics impression so formed will have the desired shape of the crown to be produced as it has been derived by way of the crown form precursor from a selected stock tooth and has been adjusted for occlusion.

This impression is then cut from the sheet placed over the cast of the stump from which the hardenable material has been removed and the margins filled with wax of a type which is normally used for the investment casting process. Thus, in the region of the margin there will be a wax coating but in the remaining region of the impression there will be a layer of shaped plastics material which will be spaced from the casting of the tooth at least in certain areas thereof. The plastics impression together with the wax margin is then removed from the cast of the stump and provided with a wax sprue and reservoir in the conventional manner. The sprued crown form of wax and plastics material is then used to produce a conventional investment casting mold and the gold crown cast in the normal way.

The process described above has two marked advantages over the conventional method of producing gold crowns. Firstly, the amount of time taken to produce the crown is considerably reduced particularly in view of the fact that it is not necessary to carry out any carving of a wax coating on the cast of the stump; this carving is both skillful and very time consuming.

Secondly, the thickness of the gold crown is governed only by the thickness of the plastics material which is used to form the impression. Thus, a much thinner crown can be achieved with the attendant saving in the amount of gold employed. It will be seen therefore that the process provides a much cheaper product which when cemented in position on the stump is indistinguishable from a conventional cast gold crown.

The use of the wax in the marginal portion will ensure that the crown has a very close fit in the important marginal areas of the stump.

The materials which are employed in producing the plaster cast and models may be those normally employed for this purpose by dental technicians. Suitable materials other than plaster may of course be used. Similarly any known material may be employed for the investment casting process which is carried out in a conventional manner.

The plastics material which is used for the first and second impressions should be capable of being formed to the desired shape when heated and should retain that shape when cooled to ambient temperature. A further requirement for the second impression is that the plastics material should be capable of being "burned-out" in the investment casting step. Poly unsaturated hydrocarbon sheets such as polypropylene and, preferably, polyethylene have been found to be suitable but it will be appreciated that other formable materials can be employed provided that they exhibit the desired characteristics outlined above.

The hardenable material which is used for producing the crown form precursor should be capable of being shaped whilst in a plastic state and preferably hardens to form a resilient material which can be distorted at least sufficiently to enable removal of the plastics impression and will subsequently regain substantially its original shape. Hardenable elastomeric materials may be employed for this purpose, particularly cold-curing elastomeric materials. One example of such a material is available commercially under the Trade Mark "IMPREGUM".

The deformable material which may be used as a backing in the deep-drawing steps may be any material which has the desired resistance to deformation at the deep-drawing temperature so as to control the plastic deformation of the heated plastics sheet to the desired degree. Such a material is available commercially and known in the art as MASTIC.

BRIEF DESCRIPTION OF THE DRAWINGS

The invention, its organization, construction and operation, will be best understood from the following detailed description taken in conjunction with the accompanying drawings, in which:

FIG. 1 is a side sectional view of a stock tooth with a first plastics impression;

FIGS. 2 and 3 are side sectional views of a trimmed first plastics impression filled with a hardenable cold-curing elastomer and pressed onto a cast model stump;

FIG. 4 is a side sectional view of a crown form precursor;

FIG. 5 is a side sectional view of a second plastics impression; and

FIG. 6 is a side sectional view of a crown form.

Although specific forms of the invention have been selected for illustration in the drawings, and although specific terms will be used in this specification in describing the features illustrated therein, these are not intended to define or to limit the scope of the invention, which is defined in the appended claims.

DESCRIPTION OF THE PREFERRED EMBODIMENTS

Reference is now made to the accompanying drawings which are a schematic representation of the steps involved in a preferred method according to the invention for producing a crown form suitable for use in producing an investment casting mold. For purposes of the following description, the steps in the below-described methods have numerals corresponding to FIGS. I through VI.

Step I shown in the drawing is an illustration of the deep-drawing of a first sheet of plastics material to the shape of a stock tooth 11 which has been selected to match the teeth surrounding the tooth to be crowned. The plastics sheet is preferably polyethylene.

The deep-drawing technique is carried out by heating a sheet of the plastics material in a frame until it is in a formable state. The stock tooth 11 is then pressed into the sheet over a supporting body of a "Mastic" material which serves to support the plastics sheet during the forming operation. The resulting first plastics impression 10 is shown in step I.

A plaster cast of the stump of the tooth which is to be crowned is produced in a conventional way. The first plastics impression 10 is trimmed from the remainder of the plastics sheet and is filled with hardenable cold-curing elastomer such as "IMPREGUM" and pressed on to the cast model stump 13 as shown in step II. This produces a layer 12 of hardenable material between the model stump 13 and plastics impression 10 and, the excess elastomer is expelled in the region of the margin 14 as can be seen in step III.

When the dentist makes an impression of the patients mouth he makes an impression of the teeth in both the upper and lower jaw as well as a specific impression of the stump of the tooth which is to be crowned. Plaster models of the teeth in the upper and lower jaw and the stump to be crowned are then made from the impressions taken by the dentist.

The assembly of the cast model stump 13, the layer of hardenable elastomer 12 and first plastics impression 10 is inserted in the plaster model of the appropriate jaw and the model of the other jaw pressed against it so that the occluding tooth 15 can bear upon the first plastics impression 10 and suitably shape the underlying layer of hardenable elastomer 12.

After the elastomer has hardened the first plastics impression 10 is removed and the excess hardened elastomer removed from the region of the margin 14 in step III and then smoothed down to give a smooth marginal area 17. This step produces the crown form precursor 16 as shown in step IV. The crown form precursor 16 is then utilized in a second deep-drawing step similar to the one employed for producing the first plastics impression 10. Again it is preferred to use a sheet of polyethylene for this purpose.

The impression is then trimmed from the plastics sheet to produce a second plastics impression 18 which will have the shape of the crown form precursor 16 which in turn has the general shape of the original chosen stock tooth 11 modified to suit the occluding tooth 15. Thus, the second plastics impression 18 will correspond to the desired shape of the crown but when it is assembled on the cast model stump 13 there will be a spacing over at least a portion thereof.

In order that the crown should fit the stump accurately further material in the form of wax is added in the marginal portions as shown in step V. The wax is smoothed down to the desired external configuration and then the second plastics impression 18 together with the wax 19 is removed from the cast model stump 13 to produce the crown form 20 shown in step VI.

This crown may then be provided with a conventional wax sprue and wax reservoir and utilized to produce the investment casting mold. Both the polyethylene and the wax are burned out to leave the mold cavity which is subsequently employed to mold the crown material such as gold to produce the crown.

It will be apparent from the above description, and particularly with reference to step V, that the crown which is produced is considerably thinner than the crown which would be produced by a conventional technique in which crown material would extend from the stump 13 to the outer profile of the second plastics impression 18. It has been found that the production of such thin crowns does not produce an inferior product as when the dentist applies the crown to the stump the space therebetween is filled with cement and the important marginal area is made to fit the stump precisely by virtue of the addition of the wax 19 as shown in step V.

The sheet of formable material may be formed by using a convenient forming technique other than the deepdrawing technique described above. Vacuum forming could be used and in this case it would be possible to vacuum form a plurality of forms in a single sheet of formable material.

The method of the invention enables a high quality crown to be produced in a relatively short time and requires less skill than the conventional method involving a carving technique. The method can be employed for producing crowns of any castable material. The thickness of the crown is, of course, predetermined by the thickness of the formed sheet, unless a crown of other than constant thickness is required, in which case material such as wax, can be added in selected areas.

The first sheet of formable material may be preformed and supplied, for example, to a dental laboratory as part of a kit for making crowns. The preformed sheet may include a number of shapes of teeth from which the technician can select a suitable form for his purpose. This avoids the technician having to carry out step I of the method and also he does not need to carry a selection of stock teeth for this purpose.

It will be appreciated that the method described above is a particularly attractive commercial method for producing crowns of a precious metal such as gold, as the amount of precious metal used is considerably less than would be used in producing an equivalent crown by a conventional technique.

I claim:

1. A method of making a form of a desired shape, for use in an investment casting technique which comprises:
   (a) forming a first sheet of formable material to a shape which approximates to the desired shape of the form;
   (b) disposing the formed shape around a layer of deformable hardenable material;
   (c) applying a compressive force to the formed shape to deform the underlaying hardenable material to a desired shape;
   (d) hardening the hardenable material to produce a form precursor;
   (e) removing the formed shape from the hardened form precursor; and
   (f) utilizing the hardened form precursor to form a second sheet of formable material into the form of the desired shape.

2. A method according to claim 1 in which the first sheet is formed by means of a deep-drawing technique.

3. A method according to claim 1 in which the second sheet is formed by a deep-drawing technique.

4. A method according to claim 3 in which additional material is added to the second formed sheet in order to produce the final desired shape of the form.

5. A method according to claim 4 in which the additional material is wax.

6. A method according to any of claim 1 in which the formable material is selected from the group, polyethylene and polypropylene.

7. A method according to claim 1 in which the hardenable material is a cold-curing elastomer.

8. A method according to claim 1 in which the form is in the shape of a crown for a tooth.

9. A method of making a crown for a tooth which comprises:
   (a) forming a first sheet of formable material to a shape which approximates to a desired shape of the crown;
   (b) applying a layer of hardenable material between a cast model of the tooth stump to which the crown is to be fixed and the formed shape from step (a);
   (c) disposing the assembly of the cast model of the tooth stump, hardenable material and formed shape in a model of the teeth surrounding the tooth to be crowned and applying a compressive force to the assembly by means of a model of the occluding tooth or teeth in the jaw opposite to that in which the tooth to be crowned is situate to deform the underlying hardenable material to a desired shape;
   (d) hardening the hardenable material to produce a crown form precursor;
   (e) removing the formed shape from the hardened crown form precursor;
   (f) utilizing the hardened crown form precursor to form a second sheet of deformable material into a crown form of the desired shape of the crown;

(g) producing an investment casting mold from the crown form of step (f) and burning out the crown form; and (h) casting the crown in the investment casting mold.

10. A method according to claim 9 in which the formable sheet is formed by means of a deep-drawing technique.

11. A method according to claim 9 in which additional material is added to the second formed sheet in order to produce the final desired shape of the form.

12. A method according to claim 11 in which the additional material is wax.

13. A method according to claim 9 in which the formable material is selected from the group polypropylene and polyethylene.

14. A method according to claim 9 in which the hardenable material is a cold-curing elastomer.

15. A method according to claim 9 in which the crown is a gold crown.

16. A method according to claim 1 in which the first sheet is formed by means of a vacuum forming technique.

17. A method according to claim 2 in which the second sheet is formed by means of a vacuum forming technique.

* * * * *